(12) United States Patent
Omata

(10) Patent No.: US 6,807,861 B2
(45) Date of Patent: Oct. 26, 2004

(54) INSTRUMENT FOR NONCONTACT MEASUREMENT OF PHYSICAL PROPERTY

(75) Inventor: Sadao Omata, Koriyama (JP)

(73) Assignee: School Juridical Person Nihon University, Tokyo (JP)

(*) Notice: Subject to any disclaimer, the term of this patent is extended or adjusted under 35 U.S.C. 154(b) by 0 days.

(21) Appl. No.: 10/240,321
(22) PCT Filed: Apr. 26, 2001
(86) PCT No.: PCT/JP01/03653
§ 371 (c)(1), (2), (4) Date: Oct. 1, 2002
(87) PCT Pub. No.: WO01/84135
PCT Pub. Date: Nov. 8, 2001

(65) Prior Publication Data
US 2003/0154793 A1 Aug. 21, 2003

(30) Foreign Application Priority Data
Apr. 28, 2000 (JP) ............... 2000-131594

(51) Int. Cl.$^7$ ............................ G01N 29/12
(52) U.S. Cl. ............... 73/627; 73/573; 73/630; 73/631
(58) Field of Search ............... 73/573, 627, 630, 73/631, 624, 579, 597

(56) References Cited

U.S. PATENT DOCUMENTS 3,741,334 A * 6/1973 Kaule ............... 73/627
5,766,137 A 6/1998 Omata ............... 73/573

FOREIGN PATENT DOCUMENTS

| EP | 0 764 842 A2 | 3/1997 |
| JP | A 2-290529 | 11/1990 |
| JP | A 6-273396 | 9/1994 |
| JP | A 9-145691 | 6/1997 |

* cited by examiner

Primary Examiner—John E. Chapman
(74) Attorney, Agent, or Firm—Oliff & Berridge, PLC

(57) ABSTRACT

A noncontact physical property measurement instrument which easily and accurately measures physical properties of an object using a nondestructive, noncontact sensor. A noncontact physical property measurement instrument 1 is provided with a transmitting section 21 and a receiving section 22. The transmitting section 21 sends a wave to an object 41 in a medium 100, and the receiving section 22 receives a wave reflected from the object 41 and the surface of a coating 42. Both the transmitting section 21 and the receiving section 22 are connected to a gain change correction circuit 13 to form a self-excited oscillating circuit 11 serving as a feedback loop. The gain change correction circuit 13 corrects the gain to the increase side according to a phase difference between the sent wave and the reflected wave, to thereby measure any changes due to a difference in physical properties of the object 41.

2 Claims, 5 Drawing Sheets

INSTRUMENT FOR NONCONTACT MEASUREMENT OF PHYSICAL PROPERTY

TECHNICAL FIELD

The present invention relates to a physical property measurement instrument which measures physical properties of an object nondestructively and without directly contacting the object.

BACKGROUND ART

As an instrument capable of ascertaining the physical properties of an object by nondestructive testing, there is, for example, the hardness measurement instrument disclosed in Japanese Patent Laid-Open Publication No. Hei 9-145691 by the present inventor. This hardness measurement instrument oscillates a contact element made to contact the surface of the object being tested and oscillates the contact element to easily and accurately measure the hardness of the object being tested according to an oscillation frequency of the contact element.

However, such a hardness measurement instruments has a problem that measurement is not possible when the contact element cannot be made to contact the surface of the test object because, for example, the object is covered with a material. In such situations, the conventional devices cannot measure the hardness or physical properties of the target object.

Even when the object is exposed, with a conventional device it is difficult to measure the hardness of the object when the contact element could not be contacted to the object under test because, for example, the target object is floating in water.

DISCLOSURE OF THE INVENTION

The noncontact physical property measurement instrument according to the present invention comprises a transmitting section which sends a wave to a test object in a medium; a receiving section which receives a wave reflected by the object; a self-excited oscillating circuit which connects the transmitting section and the receiving section to perform feedback oscillation; and a physical property measurement section which measures physical properties of the object according to an oscillation frequency of the self-excited oscillating circuit. Thus, differences in physical properties (e.g., hardness) of the object can be measured from the oscillation frequency of the self-excited oscillating circuit without directly contacting the contact element to the object to be tested. Therefore, even if the surface of the object is coated or it is otherwise not possible or difficult to directly contact the object, the physical properties of object can still be easily and accurately measured.

According to the present invention, the self-excited oscillating circuit may be provided with a gain change correction circuit which has a center frequency different from the center frequency of the self-excited oscillating circuit and increases gain in response to a change in frequency. When this is done, the sensitivity to the gain change due to the change in frequency can be enhanced, so that the physical properties of an object to be testedcan be measured more accurately.

According to the present invention, there may also be provided a storage section in which is prestored data on an interrelation between physical properties and the oscillation frequency of the self-excited oscillating circuit. Provision of such a storage section enables faster measurement of physical properties based on the value of oscillation frequency, without sacrificing accuracy.

BEST MODE FOR CARRYING OUT THE INVENTION

Figure 1:
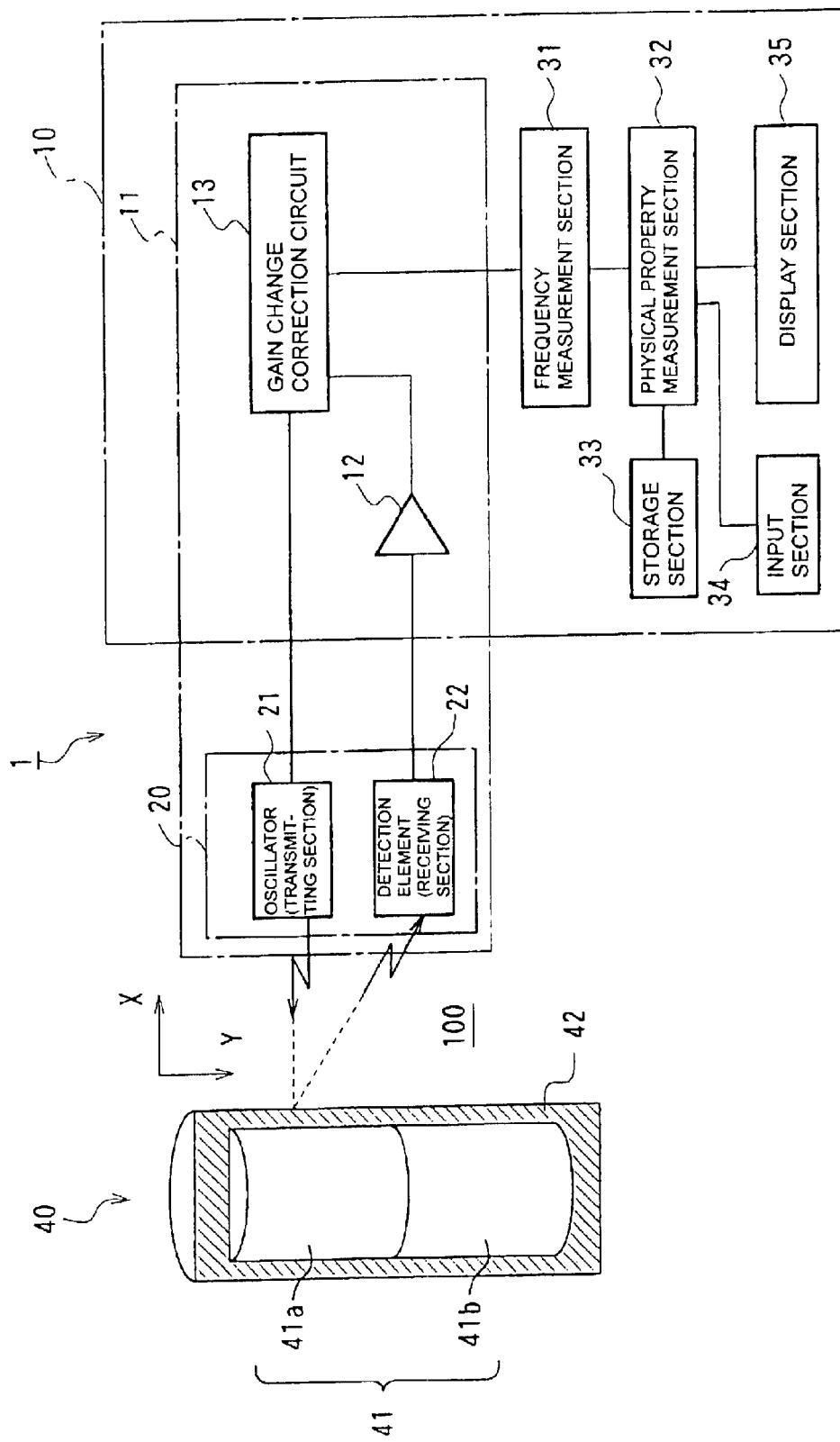
FIG. 1 is a schematic structure diagram of a noncontact physical property measurement instrument according to an embodiment of the present invention.
Figure 2:
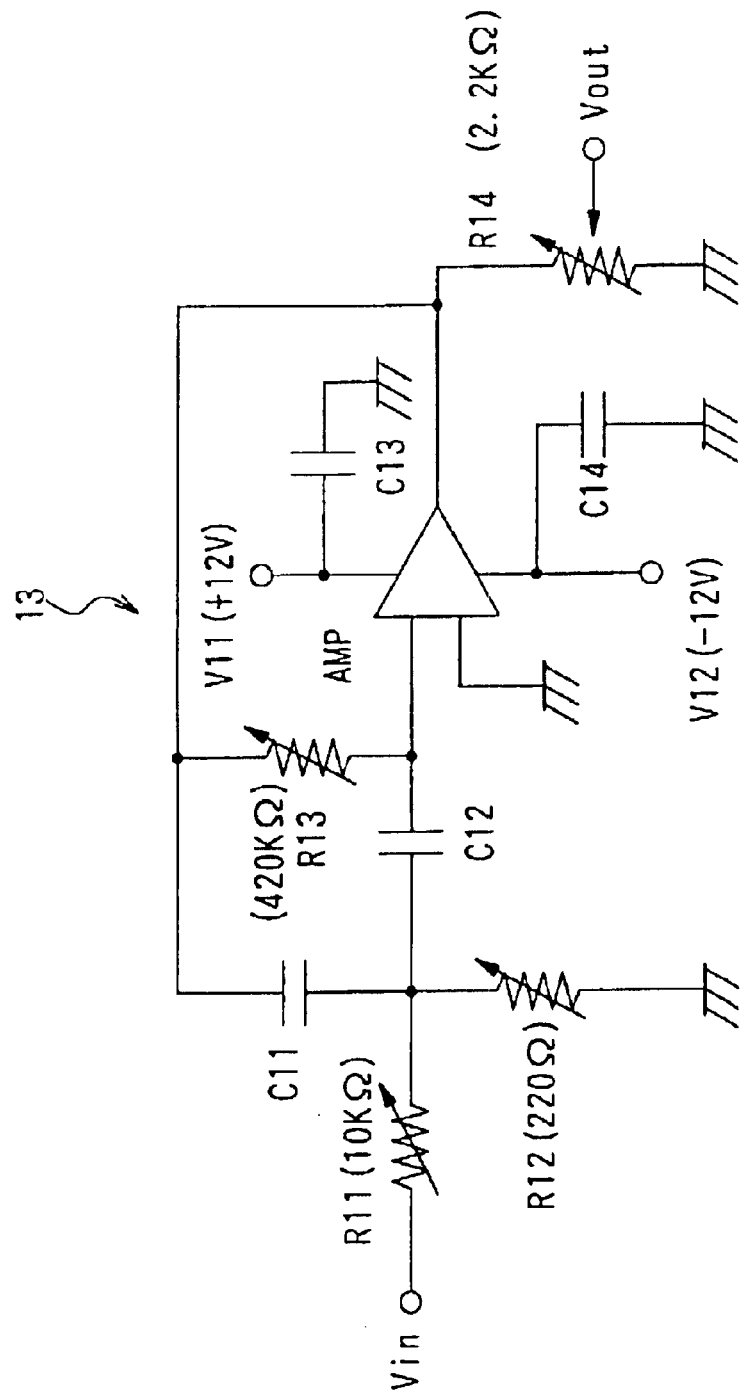
FIG. 2 is a circuitry diagram showing an example of a gain change correction circuit according to the embodiment of the present invention.

Embodiments of the present invention will be described with reference to the drawings. FIG. 1 is a schematic structure diagram of a noncontact physical property measurement instrument, and FIG. 2 is a circuitry diagram of a gain change correction circuit of the noncontact physical property measurement instrument.

System Configuration of Noncontact Physical Property Measurement Instrument

First, the system configuration of a noncontact physical property measurement instrument 1 according to a first embodiment will be described. This noncontact physical property measurement instrument 1 is provided with a control unit 10 and a sensor unit 20 and measures physical properties (e.g., hardness) of an object 41 included in an object-containing material 40 in a medium 100 (e.g.,water). The object-containing material 40 shown as an example in FIG. 1 is comprised of the object 41, which is formed of a first object 41a (aluminum rod) and a second object 41b (copper rod) which are mutually joined, and a coating 42 (silicon) which covers the exterior of the object 41.

The sensor unit 20 includes a transmitting section 21 and a receiving section 22. The transmitting section 21 (e.g., an ultrasonic oscillator) converts an electric signal from a gain change correction circuit 13 into a wave (e.g., an ultrasonic pulsed wave) and transmits the wave to the object-containing material 40 in the medium 100. The receiving section 22 (e.g., a detection element) receives a component of the wave transmitted from the transmitting section 21 reflected by the object-containing material 40 and converts the reflected wave into an electrical signal. This electrical signal is returned to the gain change correction circuit 13.

An amplification circuit 12 is disposed between the gain change correction circuit 13 and the transmitting section 21 or the receiving section 22. In the configuration of this embodiment, the amplification circuit 12 is disposed between the receiving section 22 and the gain change correction circuit 13 and amplifies the electric signal which was converted from the wave received by the receiving section 22. The amplified electric signal is input to the gain change correction circuit 13.

These gain change correction circuit 13, transmitting section 21, receiving section 22, and amplification circuit 12 are component elements of a self-excited oscillating circuit 11 serving as a feedback loop.

The gain change correction circuit 13 which is disposed within the control unit 10 has a function to adjust gain (e.g., to increase the gain in response to the increase of the frequency) in response to changes in frequency, a phase transfer function to adjust to zero an I/O combined phase difference between an input phase and an output phase of the self-excited oscillating circuit 11 to promote feedback oscillation, and a function to adjust the frequency to make the I/O combined phase difference zero and to increase a gain change in response to changes in the frequency (e.g., to increase the gain change in response to an increase in frequency).

As the gain change correction circuit 13, for example, a filter circuit having a frequency-gain characteristic such that the gain increases in response to the change in the frequency is used. FIG. 2 is a circuit diagram showing an example of the filter circuit used as the gain change correction circuit 13. This filter circuit has resistors R11, R12, R13, R14, capacitors C11, C12, C13, C14, and an amplification circuit AMP. In this example, the resistor R11 is set to 10 KΩ, the resistor R12 is set to 220Ω, the resistor R13 is set to 420 KΩ, and the resistor R14 is set to 2.2 KΩ. Power (12V) is supplied from a power-supply terminal V11 to the amplification circuit AMP and a voltage (−12V) is applied to a standard power-supply terminal V12. In the drawing, reference symbol Vin indicates a signal input terminal and reference symbol Vout indicates a signal output terminal. This filter circuit has the characteristics of a band pass filter circuit. The input terminal Vin of the gain change correction circuit 13 is connected to the output terminal of the amplification circuit 12, and the output terminal Vout is connected to the input terminal of the transmitting section 21.

Other than the above-described gain change correction circuit 13 and amplification circuit 12, the control unit 10 also has a frequency measurement section 31 which measures, for example, an oscillation frequency of the self-excited oscillating circuit 11 as a frequency of the reflected wave, a physical property measurement section 32 which measures physical properties, e.g, hardness, according to a frequency measured by the frequency measurement section 31, a storage section 33 which previously stores an interrelation between the frequency and the physical properties, an input section 34 which enters instruction input to the control unit 10, and a display section 35 which shows measured frequency values, physical property values or the like.

Basic Principle of Self-excited Oscillation

Figure 3:
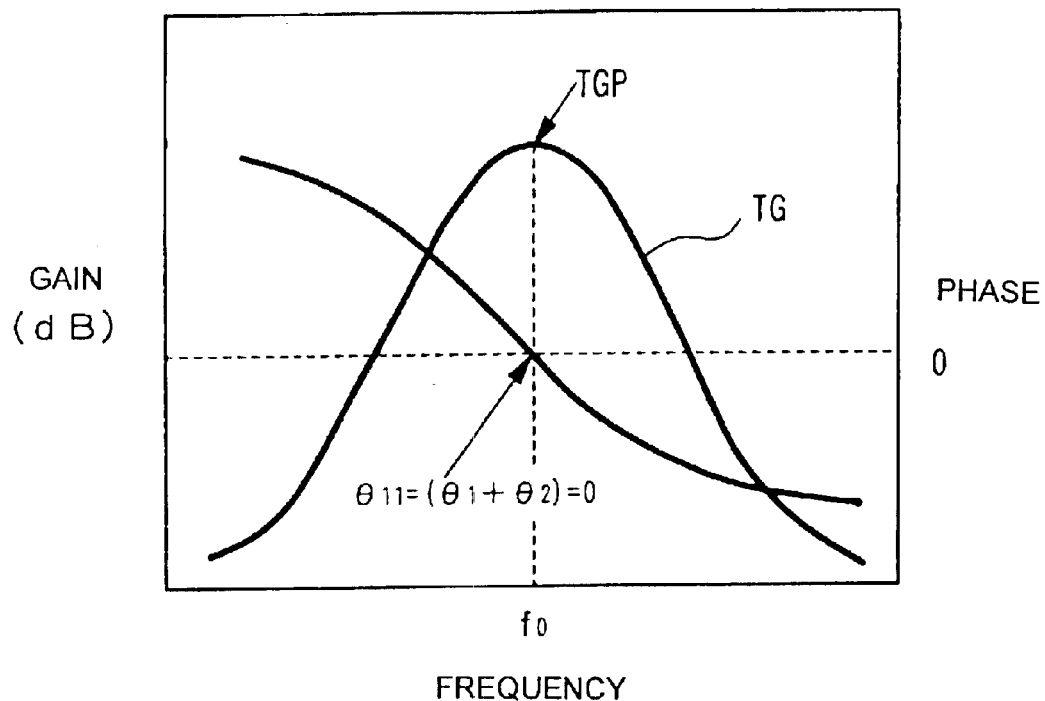
FIG. 3 is a frequency-gain-phase change characteristic curve chart showing a total frequency characteristic having combined respective frequency characteristics of a self-excited oscillating circuit and a gain change correction circuit according to the embodiment of the present invention.

Next, the basic principle of self-excited oscillation will be described. FIG. 3 is a frequency-gain-phase characteristic curve chart showing a total frequency characteristic having combined frequency characteristics of the self-excited oscillating circuit 11 and the gain change correction circuit 13. The horizontal axis indicates a frequency, and the vertical axis indicates gain and phase. A frequency-gain characteristic curve TG indicates a total frequency characteristic combining the frequency characteristic of the gain change correction circuit 13 and the frequency characteristic of the self-excited oscillating circuit 11. The frequency-gain characteristic curve TG forms a mountain-shaped curve showing that the gain rises as the frequency increases in a band of a low frequency, becomes maximum in a band of resonance frequency f0, and decreases in a high frequency band. Characteristic curve θ11 is a phase characteristic showing an I/O phase difference between an input phase and an output phase of the self-excited oscillating circuit 11.

This self-excited oscillating circuit 11 adjusts to zero the I/O phase difference of the self-excited oscillating circuit 11 at the resonance frequency f0 indicating a gain maximum value TGP of the frequency-gain characteristic curve TG. Specifically, in the self-excited oscillating circuit 11, the I/O combined phase difference θ11, which is a phase difference between a phase (input phase) θ1 of the resonance frequency to be output from the receiving section 22 and a phase (output phase) θ2 after the gain rise output from the gain change correction circuit 13 and fed back to the transmitting section 21, is adjusted to zero (θ11=θ1+θ2=0). When the adjustment of the I/O combined phase difference θ11 results in a phase difference between the input phase θ1 and the output phase θ2 of the self-excited oscillating circuit 11 including the gain change correction circuit 13, feedback is repeated until the I/O combined phase difference θ11 becomes zero, and oscillation is performed at the point when the I/O combined phase difference θ11 becomes zero. As a result, feedback oscillation of the self-excited oscillating circuit 11 is performed more securely, and the feed back oscillation can be promoted. The I/O combined phase difference θ11 is adjusted by the gain change correction circuit 13. The gain change correction circuit 13 can easily realize adjustment of the I/O combined phase difference θ11 by adjusting center frequency f2 of the frequency characteristic.

Figure 4:
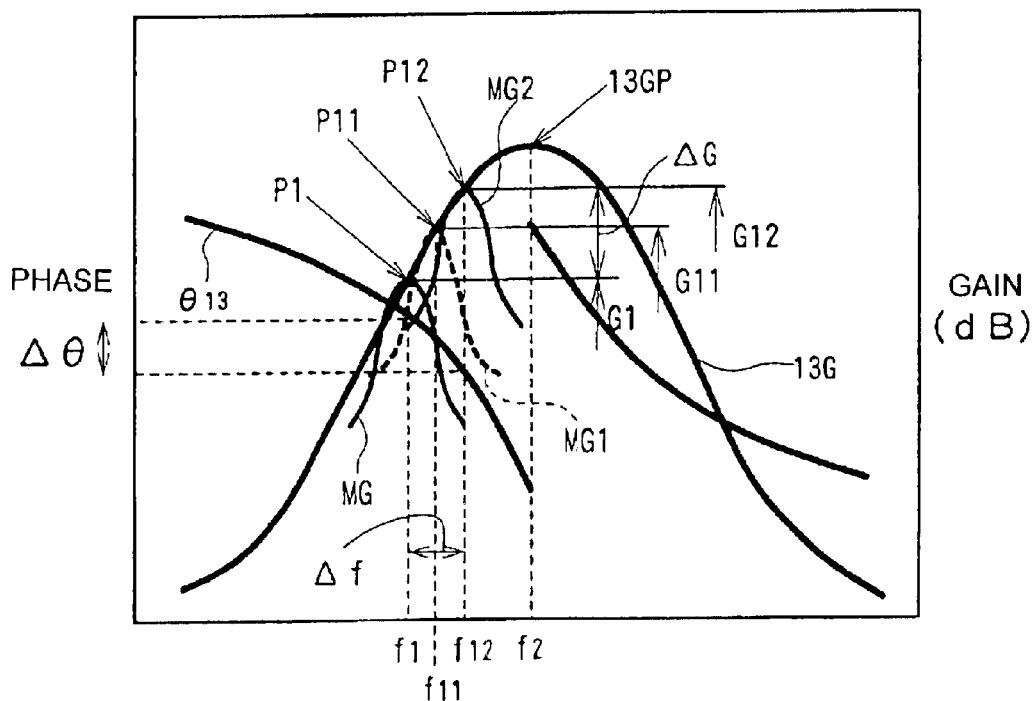
FIG. 4 is a frequency-gain-phase change characteristic curve chart showing respective frequency characteristics of the self-excited oscillating circuit and the gain change correction circuit according to the embodiment of the present invention.

FIG. 4 is a frequency-gain-phase characteristic curve chart showing respective frequency characteristics of the self-excited oscillating circuit 11 and the gain change correction circuit 13. The horizontal axis indicates a frequency, and the vertical axis indicates gain and phase. A frequency-gain characteristic curve 13G of the gain change correction circuit 13 forms a mountain-shaped curve showing that the gain rises as the frequency increases in a low frequency band, becomes maximum in a band of the center frequency f2, and decreases in a band of a high frequency. A characteristic curve θ13 is a phase characteristic showing an I/O phase difference of the gain change correction circuit 13. A characteristic curve MG is a frequency-gain characteristic curve of the self-excited oscillating circuit 11 excepting the gain change correction circuit 13. The frequency-gain characteristic curve MG forms substantially the same mountain-shaped curve as that of the frequency characteristic of the gain change correction circuit 13, although the center frequency f1, the frequency band, and the gain maximum value are different.

In this embodiment, as respectively indicated by the frequency-gain characteristic curves MG and 13G, the center frequency f1 of the self-excited oscillating circuit 11 indicted by a gain maximum value P1 and the center frequency f2 indicated by a gain maximum value 13GP of the gain change correction circuit 13 are set to frequency bands which are deliberately displaced from each other. For example, the center frequency f2 of the gain change correction circuit 13 is set to a high frequency band against the center frequency f1 of the self-excited oscillating circuit 11 so that the gain becomes higher as the physical property value of the object 41, e.g., a hardness coefficient, becomes higher.

A frequency characteristic or directional characteristic of the reflected wave received by the receiving section 22 varies according to the physical properties, e.g., hardness, of the object 41, resulting in a change in frequency, gain, phase and amplitude of the electric signal of the self-excited oscillating circuit 11. Specifically, the frequency of the self-excited oscillating circuit 11 changes (e.g., rises) from the center frequency f1 of the self-excited oscillating circuit 11 to the resonance frequency f11 according to the physical properties, e.g., hardness, of the object 41. Here, the gain maximum value of the frequency-gain characteristic curve MG of the self-excited oscillating circuit 11 changes from the gain maximum value P1 along the frequency-gain characteristic curve 13G of the gain change correction circuit 13 and to increase from the gain maximum value P1. In other words, the frequency-gain characteristic curve MG of the self-excited oscillating circuit 11 changes to a frequency-gain characteristic curve MG1, and the gain maximum value P1 changes to a gain maximum value P11, and the gain G1 changes to a gain G11, respectively.

As shown in FIG. 2, because the feedback loop by the self-excited oscillating circuit 11 contains a resistor and a capacitor, there is always a phase difference $\Delta\theta$ between the input phase $\theta 1$ and the output phase $\theta 2$ of the self excited oscillating circuit 11. Here, the gain change correction circuit 13 has a phase transfer function and adjusts to make the I/O combined phase difference $\theta 11$ of the feedback loop including the gain change correction circuit 13 zero, so that the frequency changes further more to reach a stable point of the feedback oscillation when the I/O combined phase difference $\theta 11$ becomes zero, and the gain also changes. Specifically, the frequency-gain characteristic curve MG1 of the self-excited oscillating circuit 11 changes to the frequency-gain characteristic curve MG2, and the resonance frequency f11 changes to a resonance frequency f12. In association with the change to the resonance frequency f12, the gain maximum value P11 changes to a gain maximum value P12, and the gain G11 changes to gain G12. In other words, for a portion corresponding to the phase difference $\Delta\theta$, the center frequency 11 of the self-excited oscillating circuit 11 continuously changes, e.g., increases, to the resonance frequency f12, and the gain G1 continuously changes, e.g., increases, to the gain G12. As a result, frequency variation $\Delta f$ can be obtained, and gain variation $\Delta G$ can also be obtained by the self excited oscillating circuit 11. At the point when the frequency variation $\Delta f$ and the gain variation $\Delta G$ of the self excited oscillating circuit 11 are obtained, the I/O combined phase difference $\theta 11$ becomes zero, and the self-excited oscillating circuit 11 performs feedback oscillation. In the physical property measurement instrument 1 according to this embodiment, the phase difference of the reflected wave differs from the irradiated wave according to the physical properties, e.g., hardness, of the object 41, so that the frequency variation $\Delta f$ and the phase difference $\Delta\theta$ change depending on the physical properties, and such change can be caught where it is expanded. Thus, a detection voltage sufficient for judging the physical properties of the object 41 can be obtained.

Calibration of Noncontact Physical Property Measurement Instrument

Figure 5:
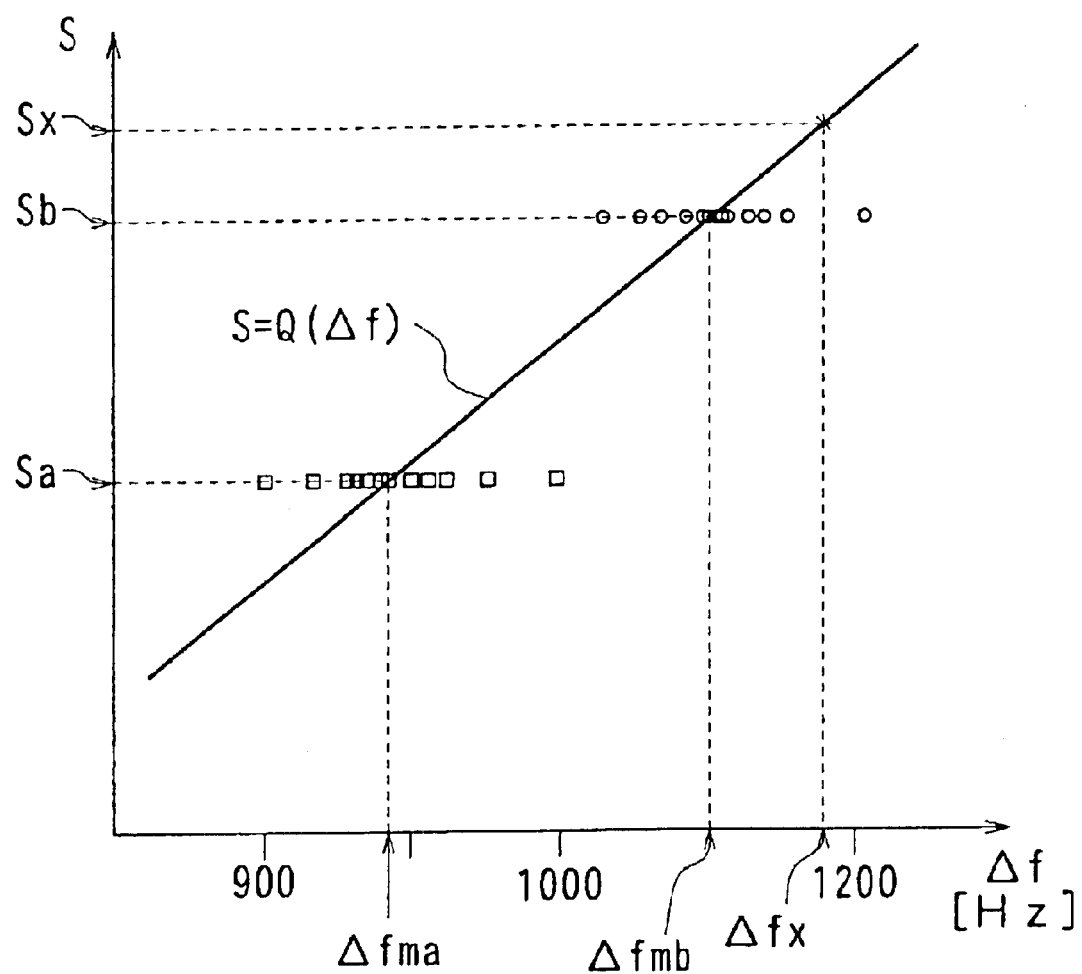
FIG. 5 is a diagram showing an example of calibrated results of physical properties measured by the noncontact physical property measurement instrument according to the embodiment of the present invention.

Next, calibration for measurement of the physical properties by the noncontact physical property measurement instrument 1 according to this embodiment will be described. FIG. 5 shows an example of interrelation between an oscillation frequency f of the noncontact physical property measurement instrument 1 calculated by calibration and the physical property (e.g., hardness S). Here, the calibration is performed on each measuring condition (e.g., the medium 100 (e.g., type, density, etc.), a temperature at the time of measurement, the coating 42 (e.g., its material or thickness) etc.). More specifically, the variation $\Delta f$ from the center frequency f1 of the oscillation frequency f under a prescribed condition and the measured physical property value, e.g., hardness value S, are measured a plurality of times on a plurality of objects 41 (e.g., the first object 41$a$, the second object 41$b$), and an interrelation between the frequency variation $\Delta f$ and the hardness value S is calculated according to the measurements as, for example, their linear function. In the example shown in FIG. 5, as a linear function S=Q ($\Delta f$) satisfying the mean values $\Delta fm$ ($\Delta fma$: the mean value on the first object 41$a$, and $\Delta fmb$: the mean value on the second object 41$b$) of the frequency variation $\Delta f$ measured on the respective objects 41 and their corresponding hardness values S (Sa: the hardness value on the first object 41$a$, and Sb: the hardness value on the second object 41$b$), their interrelations are obtained. The interrelation Q determined as described above is then stored in the storage section 33 by, for example, their coefficients (e.g., q1 and q2 when S=q1 $\Delta f$+q2). During actual measurement, the stored interrelation Q is read as, for example, the coefficients q1, q2, according to the measuring conditions input from the input section 34, and the physical property, e.g., hardness Sx, is calculated according to the interrelation Q in accordance with the measured frequency variation $\Delta fx$ and the measuring condition. Thus, the object can be estimated from the hardness Sx.

Measurement of Physical Properties

Figure 6:
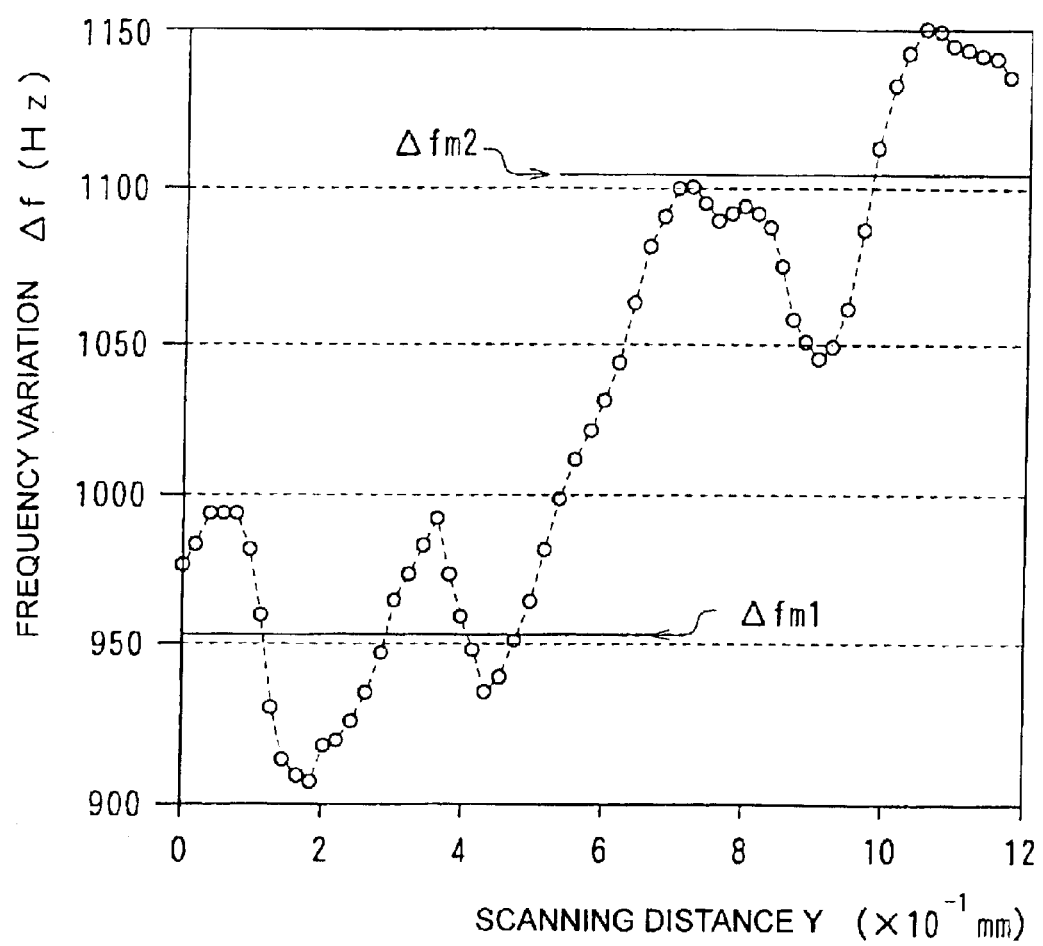
FIG. 6 is a diagram showing an example of measured results of a change in oscillation frequency of the noncontact physical property measurement instrument according to the embodiment of the present invention.

Next, measurement of physical properties by the noncontact physical property measurement instrument 1 according to this embodiment will be described. FIG. 6 shows the frequency variation $\Delta f$ obtained when the sensor unit 20 scanned in direction Y of FIG. 1 in the configuration consisting of the noncontact physical property measurement instrument 1 and the object-containing material 40 shown in FIG. 1. In FIG. 6, the horizontal axis indicates the scanning distance Y, and the vertical axis indicates the frequency variation $\Delta f$. When measuring, the object-containing material 40 and the sensor unit 20 are held separated by a prescribed distance in the X direction of FIG. 1.

In the structure shown in FIG. 1, acoustic impedance differs between a case when a wave is reflected by the surface of the first object 41$a$ and a case when it is reflected by the surface of the second object 41$b$, so that a phase lag of the reflected wave to the transmitted wave is different between them. As described above, the gain change correction circuit 13 changes the oscillation frequency f according to the phase lag, so that the frequency variation $\Delta f$ greatly varies during the scanning in the direction Y as shown in FIG. 6. From this, it can be known that the object 41 to which a wave is irradiated has a portion where the physical properties are different. Next, a mean value $\Delta fm1$ of frequency changes before the large change and a mean value $\Delta fm2$ of frequency changes after the large change of the frequency variation $\Delta f$ are calculated, and each value is compared with the interrelation Q according to the measurement conditions stored in the storage section 33 to calculate or measure the physical property value, e.g., hardness value, of the object 41, and it can be presumed from the physical property value what material is used for the object 41.

The present invention is not limited to the above embodiment. For example, although in the above embodiment the gain change correction circuit 13 is disposed between the amplification circuit 12 and the transmitting section 21, this circuit could be disposed elsewhere, such as between the receiving section 22 and the amplification circuit 12.

Also, the gain change correction circuit 13 may have a property to increase the gain when the frequency changes so to increase the voltage according to the increase in gain. Therefore, in addition to the band pass filter circuit of the above embodiment, for example, a low-pass filter circuit, a high-pass filter circuit, a notch-filter circuit, a integration circuit, a differentiation circuit, or a peaking amplification circuit can be used as the gain change correction circuit 13.

While in the above embodiment, the center frequency f2 of the gain change correction circuit was set to a frequency band higher than the center frequency f1 of the self-excited oscillating circuit 11, the frequency may be set in a low frequency band.

Although in the above embodiment the ultrasonic oscillator was used as the transmitting section, the present invention is not limited to such a configuration. Other configurations are acceptable, as long as a wave can be sent to the object 41 and the reflected wave can be received from the object 41 or the object-containing material 140. Additionally, an electromagnetic wave can also be employed as the wave to be sent. Similarly, the physical property which can be measured by the present invention is not limited to hardness.

Industrial Applicability

As described above, because with the present invention a difference in physical properties of an object can be measured as an oscillation frequency without contacting the contact element to the object, the physical properties of the object can be measured and more easily and more accurately, even when the surface of the object is coated or when direct contact with the object is otherwise difficult.

What is claimed is:

1. A noncontact physical property measurement instrument, comprising:

a transmitting section which sends a wave to an object in a medium;

a receiving section which receives a wave reflected by the object;

a self-excited oscillating circuit which connects the transmitting section and the receiving section to perform feedback oscillation; and a physical property measurement section which measures physical properties of the object according to an oscillation frequency of the self-excited oscillating circuit; and the self-excited oscillating circuit is provided with a gain change correction circuit which has a center frequency different from the center frequency of the self-excited oscillating circuit and increases the gain when the frequency changes.

2. The noncontact physical property measurement instrument according to claim 1, further comprising a storage section in which has been stored data on an interrelation between physical properties and the oscillation frequency of the self-excited oscillating circuit.

* * * * *